US005551487A

United States Patent [19]
Gordon et al.

[11] Patent Number: 5,551,487
[45] Date of Patent: Sep. 3, 1996

[54] MICRO-DISPENSER FOR PREPARING ASSAY PLATES

[75] Inventors: Gary B. Gordon, Saratoga; Scott A. Conradson, Palo Alto; Kay Lichtenwalter, San Jose, all of Calif.

[73] Assignee: Hewlett-Packard Company, Palo Alto, Calif.

[21] Appl. No.: 401,520

[22] Filed: Mar. 10, 1995

[51] Int. Cl.⁶ .............................. B65B 43/42; B67C 3/00
[52] U.S. Cl. .............................. 141/1; 141/130; 422/100; 436/180
[58] Field of Search .............................. 141/1, 231–233, 141/247, 351, 352, 356, 357, 130; 422/100; 436/180; 118/256

[56] References Cited

U.S. PATENT DOCUMENTS

| | | | |
|---|---|---|---|
| 2,874,734 | 2/1959 | Luckock et al. | 141/356 |
| 4,041,995 | 8/1977 | Columbus | 422/100 |
| 4,632,808 | 12/1986 | Yamamoto et al. | 422/100 |
| 4,699,884 | 10/1987 | Noss et al. | 422/100 |
| 5,046,539 | 9/1991 | MacLeish et al. | 422/100 |
| 5,443,791 | 8/1995 | Cathcart et al. | 436/180 |

Primary Examiner—Henry J. Recla
Assistant Examiner—Steven O. Douglas

[57] ABSTRACT

A method and apparatus for dispensing immobilized reactants onto substrates for use in generating a biological assay plate for detecting the presence of mobile reactants that bind to the immobilized reactants. The apparatus includes a dispensing bed that holds a plurality of substrates. Each potential immobilized reactant is held in a cartridge. The apparatus includes a holder that allows any of these cartridges to be used in dispensing an immobilized reactant. The apparatus includes a positioning mechanism for positioning the cartridges over each of the substrates. The positioning mechanism also allows a cartridge so positioned to be brought into contact with each of the substrates at a predetermined location on each of the substrates so as to dispense a known quantity of the immobilized reactant onto the substrate at that location. In the preferred embodiment of the present invention, the cartridges include a chamber for holding the immobilized reactant and a channel having a first end communicating with the chamber. The second end of the channel provides the exit path through which the immobilized reactant exits when the cartridge is brought into contact with the substrates.

4 Claims, 3 Drawing Sheets

5,551,487

MICRO-DISPENSER FOR PREPARING ASSAY PLATES

FIELD OF THE INVENTION

The present invention relates to microdispensers, and more particularly, to a method of preparing biological assay plates having a plurality of assay spots thereon.

BACKGROUND OF THE INVENTION

Reactions between biological molecules exhibit an extremely high degree of specificity. It is this specificity that provides a living cell with the ability to carry out thousands of chemical reactions simultaneously in the same "vessel". In general, this specificity arises from the "fit" between two molecules having very complex surface topologies. For example, an antibody binds a molecule displaying an antigen on its surface because the antibody contains a pocket whose shape is the complement of a protruding area on the antigen. This type of specific binding between two molecules forms the basis of numerous biological assays.

For example, nucleic acids are linear polymers in which the linked monomers are chosen from a class of 4 possible sub-units. In addition to being capable of being linked together to form the polymers in question, each unit has a complementary sub-unit to which it can bind electrostatically. In the case of DNA, the polymers are constructed from four bases that are usually denoted by A, T ,G, and C. The bases A and T are complementary to one another, and the bases G and C are complementary to one another. Consider two polymers that are aligned with one another. If the sequences in the polymers are such that an A in one chain is always matched to a T in the other chain and a C in one chain is always matched to a G in the other chain, then the two chains will be bound together by the electrostatic forces. Hence, an immobilized chain can be used to bind the complementary chain. This observation forms the basis of tests that detect the presence of DNA or RNA that is complementary to a known DNA or RNA chain. Such detection forms the basis of a number of medical and/or diagnostic tests.

The methods by which the binding of the mobile reactant to the immobilized component of the system is measured varies with the particular reactants. However, a significant fraction of all of the tests involve the measurement of a fluorescent dye that is associated with either the bound or mobile reactant. The dye may be attached to the reactant from the beginning of the process or it may be added through various chemical steps after the mobile and immobilized reactants have been brought into contact with one another.

Systems for medical diagnosis often involve a bank of tests in which each test involves the measurement of the binding of one mobile component to a corresponding immobilized component. To provide inexpensive test kits, systems involving a matrix of immobilized spots have been suggested. Each spot includes the immobilized component of a two component test such as described above. The fluid to be tested is typically brought into contact with the matrix. After chemical processing, the amount of fluorescence associated with each of the spots in the matrix is measured.

The matrix is typically constructed by dispensing small quantities of the immobilized component onto a substrate such as glass that has been chemically modified to bind the immobilized component. The amount of material in each spot is relatively small; however, the number of spots may be quite large. Hence, the generation of such an assay plate requires a reliable microdispenser that can place the individual spots at predetermined locations with a high degree of precision.

The dispenser must also operate without clogging over a large number of samples. In addition, the dispenser must be able to change samples quickly, as each spot in the matrix requires a different immobilized component.

Broadly, it is the object of the present invention to provide an improved dispensing system and method for fabricating assay plates having a matrix of test spots thereon.

It is a further object of the present invention to provide an assay plate dispensing apparatus that is with improved immunity to clogging.

It is a still further object of the present invention to provide a method of fabricating assay plates that is adapted to the large number of different immobilized species that must be applied to each assay plate.

These and other objects of the present invention will become apparent to those skilled in the art from the following detailed description of the invention and the accompanying drawings.

SUMMARY OF THE INVENTION

The present invention comprises a method and apparatus for dispensing immobilized reactants onto substrates for use in generating a biological assay plate for detecting the presence of mobile reactants that bind to the immobilized reactants. The apparatus includes a dispensing bed that holds a plurality of substrates. Each potential immobilized reactant is held in a cartridge. The apparatus includes a holder that allows any of these cartridges to be used in dispensing an immobilized reactant. The apparatus includes a positioning mechanism for positioning the cartridges over each of the substrates. The positioning mechanism also allows a cartridge so positioned to be brought into contact with each of the substrates at a predetermined location on each of the substrates so as to dispense a known quantity of the immobilized reactant onto the substrate at that location. In the preferred embodiment of the present invention, the cartridges include a chamber for holding the immobilized reactant and a channel having a first end communicating with the chamber. The second end of the channel provides the exit path through which the immobilized reactant exits when the cartridge is brought into contact with the substrates. The channel preferably includes a cylindrical member having an enlarged region that extents into the chamber so as to prevent the cylindrical member from leaving the channel via the second end. The cylindrical member extends from the second end of the channel when the enlarged region is in contact with the first end of the channel, the enlarged region being displaced from the second end when the portion of the cylindrical member that extends from the second end is brought into contact with the substrate.

DETAILED DESCRIPTION OF THE INVENTION

Figure 1:
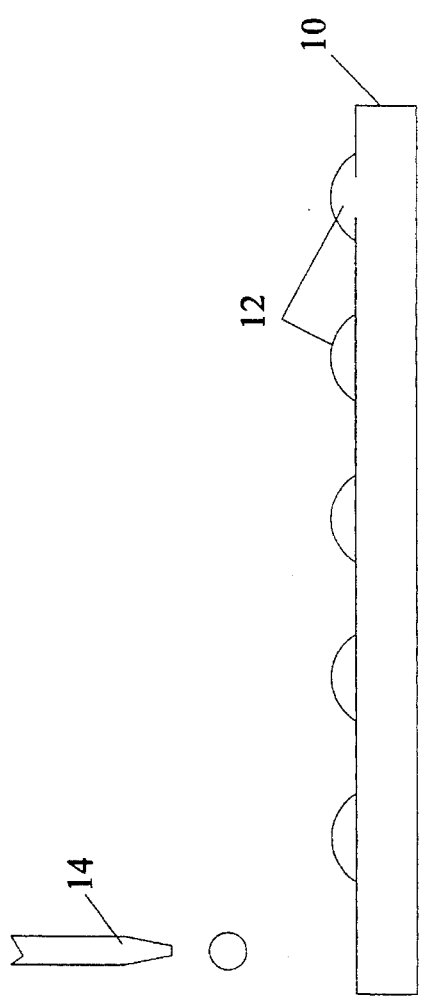
FIG. 1 is a side view of a matrix of test spots that can be generated using the present invention.
Figure 2:
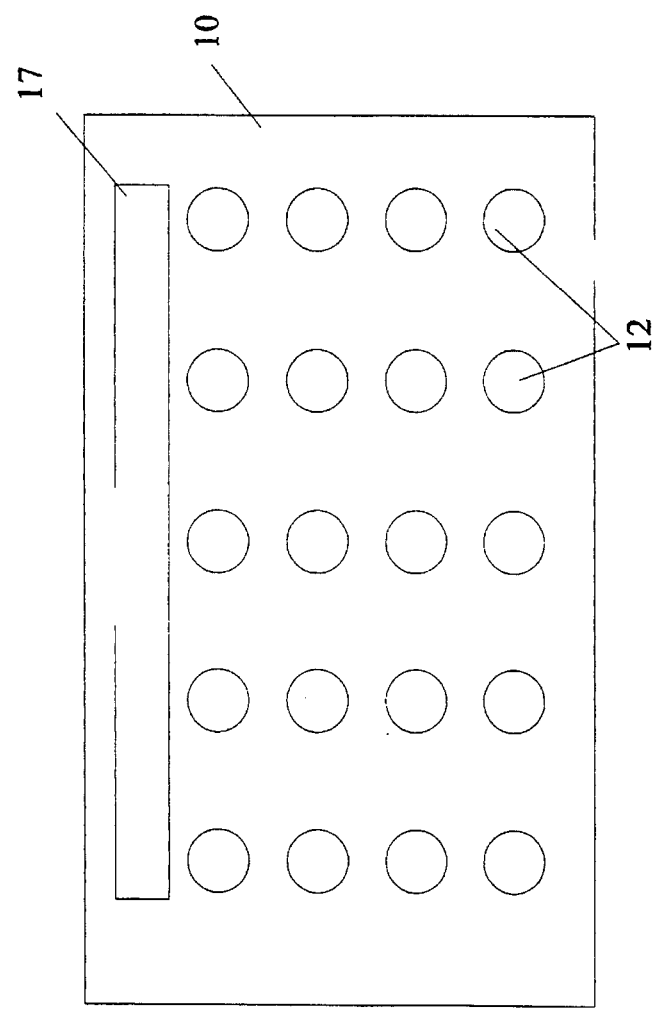
FIG. 2 is a top view of the matrix shown in FIG. 1.

The present invention may be more easily understood with reference to FIGS. 1 and 2 which are side and top views of a matrix of test spots 12 deposited on a substrate 10. The individual spots are typically dispensed by a dis ng apparatus 14. Each test spot includes one member of a pair of chemical structures that will bind to one another if brought into contact with one another. The chemical species included in the test spot will be referred to as the immobilized species. The other member of the pair will be referred to as the mobile species.

The immobilized species is typically deposited on substrate 10 in a carrier liquid after chemically modifying the substrate surface to bind the immobilized species or a precursor thereof. For the purposes of this discussion, the term immobilized species includes precursors of the actual immobilized species in the case in which the precursor is first bound to the substrate and then converted chemically into the immobilized species.

In principle, each spot includes a different immobilized species or concentration thereof that will become attached to substrate 10 when the carrier liquid evaporates. One prior art method for preparing assay plates involves coating a glass substrate with an organo-silane having active groups that will covalently bind the immobilized component when the later is dispensed onto the substrate in an appropriate carrier liquid. The presence of a target species is determined by measuring the amount of material bound to the corresponding test spot when a solution to be tested is brought into contact with the test spot. Test plates such as that shown in FIGS. 1 and 2 are designed to test for a plurality of mobile species simultaneously.

It will be appreciated from the above discussion that the apparatus that dispenses the immobilized species must be capable of accessing a large number of separate immobilized species containers and of dispensing small quantities solutions from each container at precise locations on the surface of the substrate.

Figure 3:
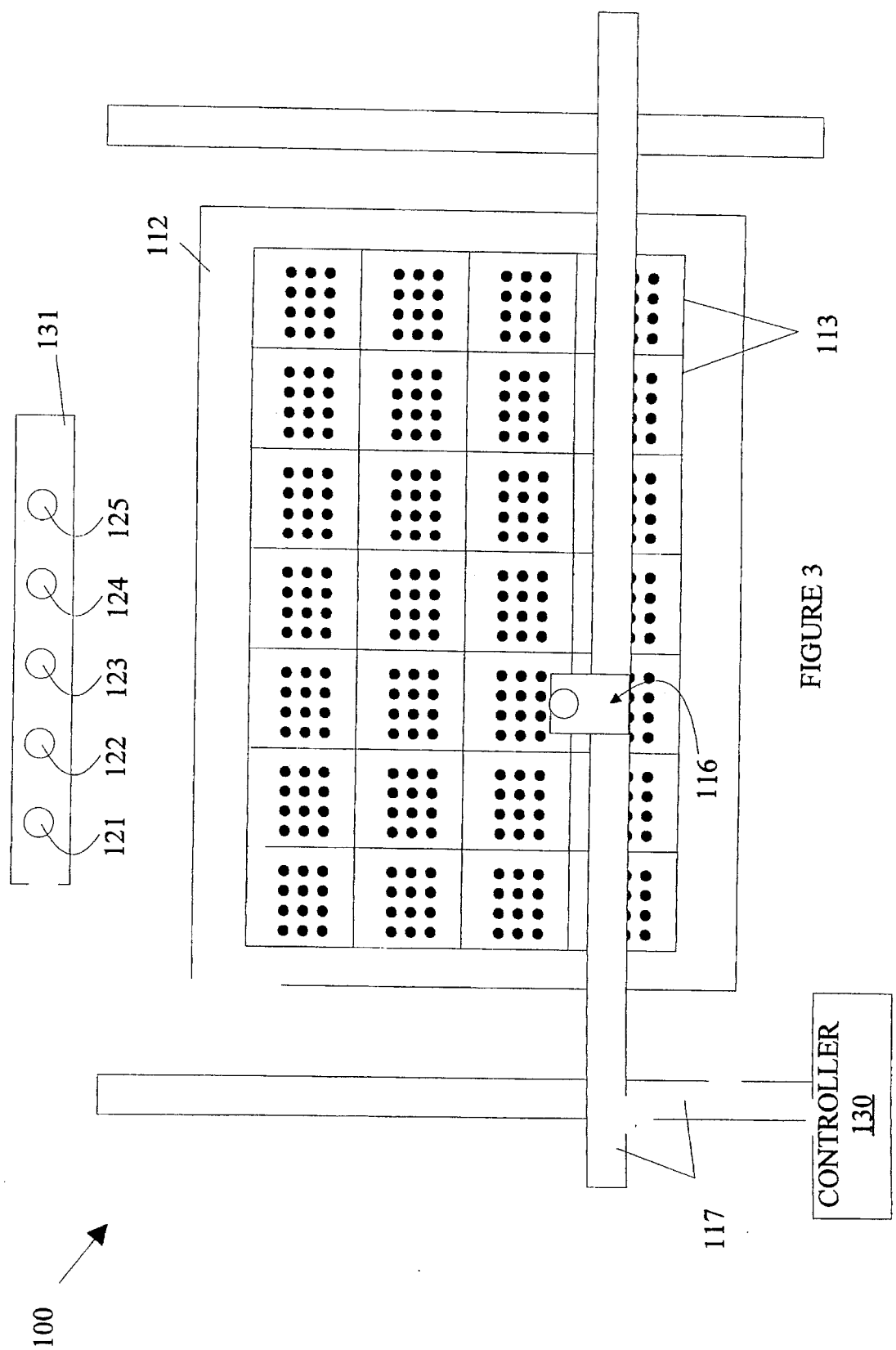
FIG. 3 is a top view of a dispensing apparatus according to the present invention.

The present invention utilizes a method and apparatus similar to a pen plotter for dispensing the immobilized species. Refer now to FIG. 3 which is a top view of a dispensing apparatus 100 according to the present invention. The bed 112 of the dispenser holds a number of substrates 113 which are to receive spots of different immobilized species. The solution corresponding to a particular concentration of an immobilized species is stored in a cartridge which is accessible to pickup arm 116. Exemplary cartridges are shown at 121–125. Pickup arm 116 rides on an XY carriage 117 that allows pickup arm 116 to be positioned over any point in bed 112. Pickup arm 116 also includes a vertical actuator that allows pickup arm 116 to be moved vertically with respect to bed 112 thereby allowing the end of a cartridge to be touched to the surface of an assay substrate on bed 112.

In operation, controller 130 stores the pattern of spots to placed on each substrate 113. For each type of spot, controller 130 causes arm 116 to pickup the corresponding cartridge and to touch it to each substrate at the corresponding spot. When all substrates have been spotted, arm 116 replaces the cartridge in its holder 131 and pickups up the next cartridge.

Figure 4:
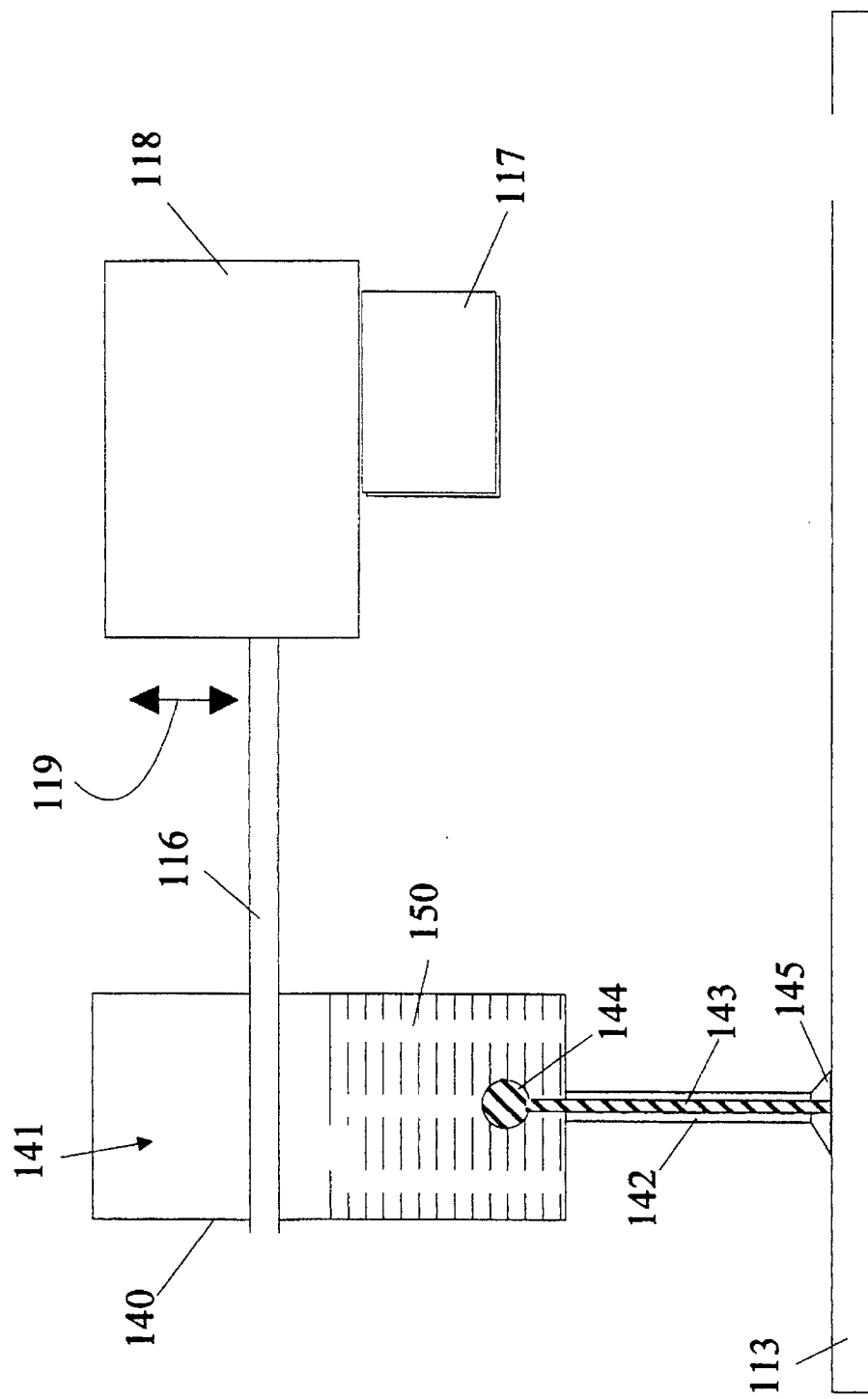
FIG. 4 is a cross-sectional view of a cartridge according to the present invention mounted in the pickup arm of the dispensing apparatus shown in FIG. 3.

Refer now to FIG. 4 which is a cross-sectional view of a cartridge 140 mounted in pickup arm 116. Pickup arm 116 is attached to XY carriage 117 via a vertical actuator 118 that allows cartridge 140 to move vertically with respect to substrate 113 as indicated by the arrows at 119. In the preferred embodiment of the present invention, cartridge 140 comprises a chamber 141 for holding the solution 150 to be spotted on the various substrates. A channel 142 connects chamber 141 to the substrate 113 when the end of channel 142 is touched to the substrate. A wire, or other cylindrical object, 143 having a bulb 144 on the end thereof passes through channel 142 is located in channel 142. When the end of channel 143 or wire 143 is in contact with the surface of a substrate, bulb 144 is lifted thereby allowing liquid to flow from chamber 141 through channel 142 onto the substrate as shown at 145. The amount of liquid that flows will, in general, depend on the surface characteristics of the substrate, the diameters of wire 143 and channel 142, the properties of the solution being dispensed, and the contact time. However, for any given combination of these factors, the controller can be calibrated to provide the required contact time for dispensing the desired amount of liquid.

In addition to preventing liquid from flowing from chamber 141 when the cartridge is not in contact with the substrate, wire 143 cleans channel 142 each time it is moved through the channel in response to the cartridge assembly being lowered onto a substrate. This cleaning action reduces the number of clogs encountered during the dispensing operations thereby substantially reducing the error rate of the dispensing apparatus.

Various modifications to the present invention will become apparent to those skilled in the art from the foregoing description and accompanying drawings. Accordingly, the present invention is to be limited solely by the scope of the following claims.

What is claimed is:

1. An apparatus for dispensing immobilized reactants onto substrates for use in generating biological assay plates for detecting the presence of mobile reactants that bind to said immobilized reactants, said apparatus comprising:

a dispensing bed for holding a plurality of substrates;

means for holding a plurality of cartridges, each said cartridge containing one of said immobilized reactants or a precursor thereof;

means for positioning one of said cartridges over each of said substrates;

means for bringing said positioned cartridge into contact with each of said substrates at a predetermined location on each of said substrates so as to dispense a known quantity of said immobilized reactant onto said substrate at said location.

2. The apparatus of claim 1 wherein one of said cartridges comprises:

a chamber for holding said immobilized reactant; and a channel having a first end communicating with said chamber and a second end through which said immobilized reactant exits when said cartridge is brought into contact with said substrates, said channel having a cylindrical member therein, said cylindrical member including an enlarged region that extends into said chamber so as to prevent said cylindrical member from leaving said channel via said second end, said cylindrical member extending from said second end of said channel when said enlarged region is in contact with said first end of said channel, said enlarged region being displaced from said second end when said cylindrical member that extends from said second end is brought into contact with said substrate.

3. A method for dispensing immobilized reactants onto substrates for use in generating biological assay plates for detecting the presence of mobile reactants that binds to said immobilized reactants, said comprising the steps of:

placing said substrates on a dispensing bed that holds a plurality of substrates;

accessing one of a plurality of cartridges, each said cartridge containing one of said immobilized reactants;

positioning one of said cartridges over one of said substrates;

bringing said positioned cartridge into contact with each of said substrates at a predetermined location on each of said substrates so as to dispense a known quantity of said immobilized reactant onto said substrate at said location.

4. The method of claim 3 wherein one of said cartridges comprises:

a chamber for holding said immobilized reactant; and a channel having a first end communicating with said chamber and a second end through which said immobilized reactant exits when said cartridge is brought into contact with said substrates, said channel having a cylindrical member therein, said cylindrical member including an enlarged region that extends into said chamber so as to prevent said cylindrical member from leaving said channel via said second end, said cylindrical member extending from said second end of said channel when said enlarged region is in contact with said first end of said channel, said enlarged region being displaced from said second end when said cylindrical member that extends from said second end is brought into contact with said substrate.

\* \* \* \* \*